United States Patent [19]

Lawson

[11] Patent Number: 5,324,347
[45] Date of Patent: Jun. 28, 1994

[54] COMPOSITION AND METHOD

[75] Inventor: John R. Lawson, Middleton, England

[73] Assignee: Imperial Chemical Industries plc, London, United Kingdom

[21] Appl. No.: 868,098

[22] Filed: Apr. 14, 1992

[30] Foreign Application Priority Data

Apr. 18, 1991 [GB] United Kingdom ............... 9108222

[51] Int. Cl.$^5$ .............................................. C09D 5/08
[52] U.S. Cl. ............................ 106/14.15; 106/14.05; 106/14.41; 106/14.42; 106/14.44; 252/389; 252/393; 252/394; 427/384; 427/388.4; 427/430.1
[58] Field of Search ............... 106/14.05, 14.15, 14.16, 106/14.41, 14.42, 14.44, 430.1; 252/387, 393, 394; 427/384, 388.4

[56] References Cited

U.S. PATENT DOCUMENTS

| | | | |
|---|---|---|---|
| 2,998,452 | 8/1961 | Bruson et al. | 564/388 |
| 3,285,991 | 11/1966 | Sellers | 528/99 |
| 3,728,281 | 4/1973 | Marks et al. | 106/141.6 |
| 3,935,160 | 1/1976 | Kline | 524/248 |
| 4,136,238 | 1/1979 | Hilterhaus et al. | 252/511 |
| 4,433,015 | 2/1984 | Lindert | 427/388.4 |
| 4,457,790 | 4/1984 | Lindert et al. | 106/14.12 |
| 4,466,840 | 8/1984 | Frank et al. | 106/14.15 |
| 4,720,536 | 1/1988 | House et al. | 528/60 |
| 4,952,732 | 8/1990 | Speranza et al. | 564/390 |

FOREIGN PATENT DOCUMENTS

| | | |
|---|---|---|
| 0276072 | 7/1988 | European Pat. Off. |
| 2216733 | 11/1973 | Fed. Rep. of Germany |
| 2518192 | 11/1976 | Fed. Rep. of Germany |
| 877062 | 9/1961 | United Kingdom |

OTHER PUBLICATIONS

Leonte et al., "Chemical Abstracts", vol. 105, No. 18, Abstract No. 155097x (Nov., 1986) p. 116.
Dickson et al., Inorganic Chemistry, vol. 13, No. 6, (1974) pp. 1301–1306.
Mandal, et al., Journal of the Chemical Society, Calton Transactions, No. 6 (1986) pp. 1175–1180.
Kochanova et al., Cjhemical Abstracts, vol. 77, No. 2, Abstract No. 6457r (Jul. 1972) p. 51.

Primary Examiner—Anthony Green
Attorney, Agent, or Firm—Cushman, Darby & Cushman

[57] ABSTRACT

A composition comprising at least one compound which is a 2,6-bis hydroxyalkylamino methyl phenol. The composition is typically water-based and certain of the compounds are novel. The composition or the compound may be deposited onto a metal surface. The coated metal surface can have corrosion inhibiting and-/or adhesion promoting characteristics.

7 Claims, No Drawings

COMPOSITION AND METHOD

This invention relates to a composition, and a method which is useful in providing a corrosion inhibiting and-/or adhesion promoting coating to a metal surface, and, in particular to the treatment of zinc, zinc-coated and phosphated steel surfaces. The invention also relates to new compounds.

Metal surfaces are known to corrode under moist conditions, especially in the presence of salts. Many methods exist for the protection of such surfaces of which the simplest is a paint coating. This, however, is not particularly satisfactory, often because the surface of the metal has already been adversely affected. This leads to poor adhesion of any paint film which is subsequently applied, resulting in cracking and flaking of the film from the metal surface.

In the case of iron and steel, it is common to coat the surface with a sacrificial metal such as zinc. Whilst this provides protection to the iron or steel, the surface coating itself is still prone to corrosion and does not alleviate the problems resulting from poor paint adhesion.

More sophisticated methods have consequently been developed such as phosphating the surface. This treatment forms a surface layer of metal phosphate which greatly improves the resistance to corrosion and at the same time provides for better adhesion of paint films. The process is, however, expensive and time consuming requiring both precise control of the phosphating process itself and protracted rinsing stages to ensure that the surface accepts any subsequent paint film and that a satisfactory bond is formed between the paint film and the metal surface. Often metal surfaces are given a further treatment after the phosphation stage which involves exposure to solutions containing hexavalent chromium salts. Again, such processing requires special equipment and precisely controlled conditions, and is further complicated by the need to ensure that no chromium enters the environment, since chromium (VI) is highly toxic and must not be allowed to enter into drinking water.

More recently, attention has been focused on the use of special chemicals which are capable of bonding to the metal surface and which may be further functionalised to improve the adhesion with any paint film which may be subsequently applied. Such chemicals include phenols, oximes and substituted o-hydroxy benzylamines. The latter class of chemicals have found many diverse uses across a wide range of industries as summarised in European patent application EP 276072. However, it is only recently that compounds of this type have been found useful for protecting metal surfaces.

Thus, EP 276072 discloses and claims aqueous, acidic compositions which are useful to deposit a corrosion inhibiting coating on a metal substrate. The composition has a pH between 2 and 6, and comprises at least 0.01% by weight of a water-soluble or water-dispersible metal-chelating compound of general formula:

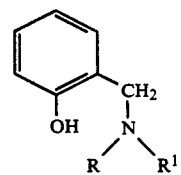

wherein R is an alkanol moiety selected from ethanol and propanol moieties and $R^1$ is H, alkyl, aryl or hydroxyalkyl. The phenol ring and alkanol moieties may be further substituted with non-interfering functionality, which is defined as functionality that would not substantially interfere with the intended use of the compounds as described in the specification. These systems are also discussed by Siegl et al in Proc. American Chem. Soc. Division of Polymeric Materials; Science and Engineering Spring Meeting 1989, Dallas, Tex. Vol. 60, 705-708.

Steric effects introduced by substituents in the chelant molecule can have a dramatic effect and can markedly influence the manner in which the molecule interlocates in the surface of the substrate.

Compounds which contain more than one chelating group in the molecule are known, such as the product formed by reacting 2 moles of 2-(methylamino)ethanol with 1 mole 2,2-bis(4-hydroxyphenyl)propane in the presence of formaldehyde. This results in a compound which is mono-substituted in each of the two aromatic phenol rings, and consequently the method by which it chelates with a metal surface does not significantly differ from that of other mono substituted ortho-hydroxy-benzylamines.

Stable aqueous compositions have also been disclosed and claimed in U.S. Pat. No. 4,433,015 assigned to Parker Chemical Company which comprise an effective amount of a water soluble or water dispersible compound of a polymer of structure:

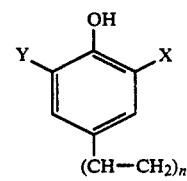

wherein n is from 2 up to a number at which the polymer is not water soluble or water dispersible, and X and Y can, independently, be amongst other things hydrogen or a group $-CR^1R^2-NR^3R^4$, wherein $R^1$ and $R^2$ can be hydrogen and $R^3$ and $R^4$ can be hydrogen, alkyl and hydroxyalkyl and at least one of X or Y is $-CR^1R^2NR^3R^4$. In the examples of U.S. Pat. No. 4,433,015, poly 4-vinylphenol of molecular weight 5000 is reacted with either N-methylaminoethanol or diethanolamine in the presence of excess formaldehyde. The examples disclose the reaction of 1 mole of amine for each equivalent of monomer unit, such that under the reaction conditions the average number of aminomethyl groups introduced into each phenol ring of the polymer repeating unit does not exceed one. Similar related compounds are also disclosed in the compositions claimed U.S. Pat. No. 4,457,790 also assigned to Parker Chemical Company.

We have now found that certain phenols which contain substituted aminomethyl groups in both the 2 and 6 positions provide a dramatically superior protection against surface corrosion compared with known compounds of this type.

According to the present invention there is provided a composition comprising
a) a liquid solvent or dispersant or a surface coating composition and
b) a 2,6-bis(substituted aminomethyl)phenol More specifically, the 2,6-bis(substituted aminomethyl)phenol is a compound of general formula (I).

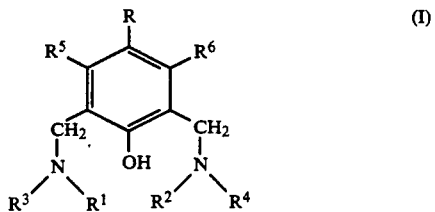

wherein:
R is hydrogen, halogen, hydrocarbyl, hydrocarbyloxy, hydrocarbylcarbonyl, hydrocarbylsulphonyl, hydrocarbylamino, hydrocarbylamido, hydrocarbyloxycarbonyl or hydrocarbylcarbonyloxy, wherein the hydrocarbyl moiety contains up to 50 carbon atoms, and may be substituted by one or more hydroxy, halogen, amino, mercapto, ether, thioether, carbonyl, sulphonyl, nitro or ester groups or a mixture thereof;
$R^1$ and $R^2$ are, independently, amino lower alkyl, mercapto lower alkyl, and hydroxy lower alkyl;
$R^3$ and $R^4$ are, independently, hydrogen, alkyl or substituted alkyl; and
$R^5$ and $R^6$ are, independently, hydrogen, halogen or lower alkoxy, or one or both of $R^5$ and $R^6$ together with R and the two ring carbon atoms may themselves form an optionally substituted ring system, and preferably, $R^5$ and $R^6$ are both hydrogen.

Preferably $R^1$ and $R^2$ are both the same. Preferably $R^3$ and $R^4$ are both the same. In one preferred embodiment, $R^1$, $R^2$, $R^3$ and $R^4$ are all the same.

The term ester means optionally substituted hydrocarbyloxycarbonyl or optionally substituted hydrocarbylcarbonyloxy groups.

In another preferred embodiment, where R is hydrocarbyl it is an alkyl chain containing up to 12 and especially not more than 10 carbon atoms. These chains may be linear or branched, and may also be mixtures. Particularly important are the mixed alkyl isomers which are commercially available as alkyl phenols. Specific examples of preferred alkyl groups are methyl, ethyl, n-butyl, t-butyl, t-octyl, n-heptyl, n-octyl and isomeric mixed nonyl.

The substituted lower alkyl groups as represented by $R^1$ and $R^2$ are those containing up to 4 carbon atoms. When $R^1$ and $R^2$ are substituted alkyl it is preferably hydroxy lower alkyl. Examples of hydroxy lower alkyl are 2-hydroxyethyl and 2-hydroxypropyl. Examples of amino lower alkyl and mercapto lower alkyl are 2-aminoethyl and 2-mercaptoethyl.

Where $R^3$ and $R^4$ are alkyl or substituted alkyl, the alkyl group may contain up to 12 carbon atoms, and especially up to 8 carbon atoms. It is particularly preferred that the alkyl or substituted alkyl group contains up to 4 carbon atoms, and is particularly methyl or ethyl, 2-hydroxyethyl, 2-mercaptoethyl, 2-aminoethyl or 2-hydroxypropyl.

Lower alkoxy as represented by $R^5$ and $R^6$ refers to substituents containing up to 4 carbon atoms and includes methoxy and ethoxy.

The term halogen includes fluorine, chlorine, and bromine, and especially chlorine.

In another particular embodiment of the invention, where R is hydrocarbyl substituted by amino it is a group —$CH_2NR^7R^8$, where $R^7$ and $R^8$ are, independently, hydrogen, alkyl or substituted alkyl provided that at least one of $R^7$ and $R^8$ is not hydrogen. Thus, in yet another embodiment, $R^1$, $R^2$ and $R^7$ when present are the same, and $R^3$, $R^4$ and $R^8$ when present are the same. $R^1$ to $R^4$ and $R^7$ and $R^8$ may all be the same.

As examples of compounds formed when $R^5$ and/or $R^6$ together with R and the ring carbon atoms to which they are attached form a ring, there may be mentioned derivatives of hydroxyquinoline, naphthols, and hydroxytetrahydroquinolines.

In another preferred embodiment of the invention where R is substituted hydrocarbyl, substituted hydrocarbyloxy, substituted hydrocarbylcarbonyl or substituted hydrocarbylsulphonyl, the substitutent itself may be a derivative of 2,6-bis(substituted aminomethyl)-phenol.

There are thus provided compositions wherein component (b) is a compound of general formula (II)

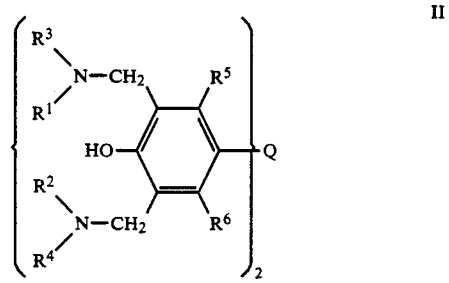

wherein:
$R^1$ to $R^4$ are as previously defined;
$R^5$ and $R^6$ are, independently, hydrogen, halogen or lower alkoxy; and
Q is a direct bond or a divalent linking group. When Q is a divalent linking group, it is preferably a $C_{1-6}$ alkylene group, for example, methylene or a substituted alkylene group, for example, dimethylmethylene, an oxygen atom, or a carbonyl or sulphonyl group.

Examples of such compounds include derivatives of 4,4'-dihydroxy biphenyl, 4,4'-dihydroxy diphenylmethane, 4,4'-dihydroxydiphenylether, 4,4'-dihydroxybenzophenone, 4,4'-dihydroxydiphenylsulphone, 2,2-bis(4-hydroxyphenyl)propane, 2,2-bis(4-hydroxyphenyl)pentane and 1-phenyl-1,1-bis(4-hydroxyphenyl)ethane.

Component a) may be a liquid in which component b) is dissolved or dispersed. Suitable liquids include aliphatic, cycloaliphatic and aromatic hydrocarbons, halogenated hydrocarbons, alcohols, esters and ketones, many of the compounds which are component b) being soluble in such liquids. Alternatively, the liquid can be water in which the compounds which are component b) are generally insoluble and hence, when component a) is water, the composition is generally a dispersion of component b) in water. Alternatively, the liquid may be a mixture such as an aqueous alcohol. If a liquid dispersant is used, this may include a suitable surfactant to aid dispersion of component b) in the liquid. Component a) may be a lubricating material, for example liquid paraffin or a synthetic polyalkylene glycol lubricant.

The composition is, however, preferably water-containing. When water-containing the composition can have a value between pH 0.5 and 12, although it is preferred that the pH value is below 7. This preferred pH value can be obtained by adding suitable amounts of strong organic acid, such as citric, tartaric or acetic acid, or by adding strong inorganic acid such as hydrochloric, sulphuric, phosphoric or sulphamic acid. Preferably, inorganic acids are used, including mixtures thereof. The actual pH used varies with the composition and is selected to provide the optimum covering and adhesion of the coating to the surface of the metal substrate.

In addition to containing an acid or acids, the water-containing composition may also contain other adjuvants such as known corrosion inhibitors, adhesion promoters, solubilizers, dispersants, or pigments. The composition may also contain lower alcohols as co-solvents such as methanol, ethanol, or isopropanol.

Alternatively, component a) is a surface coating composition, for example a film forming binder system. The film forming binder system which can be used as component (a) of the coating composition may be a paint (primer), a lacquer; a resin or other protective coating. Thus, component (a) may be a solvent-based surface coating composition, for example a cellulose/solvent based primer paint such as those used for car "touch-up" paints. The compound which is component (b) of the coating composition is generally soluble to at least some extent in the solvents used for such primers and typically is added as a solid when being incorporated into such a primer paint system. Alternatively, component (a) may be an aqueous emulsion surface coating system, for example a primer or protective coating based on polymer latices such as for example acrylic and styrene/acrylic latices and vinyl acrylic copolymer latices including acrylate modified vinyl chloride vinylidene chloride copolymer latices, and the compound which is component (b) may be used as a dispersion or suspension in such aqueous systems. The surface coating composition may be an alkali-removable protective coating composition of the addition polymer type in which the polymer contains carboxyl groups.

The film forming binder system which may be used as component (a) of the composition preferably contains an organic polymer and in general any such polymer used in the paint industry may be included in the composition. Thus, the suitable film forming binders include, for example, an alkyd resin, an epoxy resin, an oleoresin, a latex rubber, a chlorinated rubber, a vinyl resin such as polyvinylacetate or polyvinyl butyral, a polyurethane, a polyester, an organic or inorganic silicate, a polyamide or an acrylic polymer. It will be appreciated that the composition can include two or more compatible film forming polymers. The composition may also include an extender or plasticising resin, such as a hydrocarbon resin, or a coal tar derivative.

The film forming binder system which may be used as component (a) of the coating composition of the present invention can include homopolymers and copolymers of the following:
vinyl chloride
vinylidene chloride,
vinyl esters of alkanoic acids having from 1 to 18 carbon atoms in the alkyl group, especially vinyl acetate, alkyl acrylates and methacrylates having from 1 to 18 carbon atoms in the alkyl group, acrylamide and substituted acrylamides, acrylonitrile, and methacrylonitrile,
monoethylenically unsaturated hydrocarbons, for example ethylene, isobutene, styrene and alpha-methyl styrene.

Example of polymers usable when component (a) is a film forming binder system are "acrylic polymers", by which is meant those polymers comprising predominantly units of alkyl acrylates and/or methacrylates having from 1 to 12 carbon atoms in the alkyl group, sometimes containing an acid functionally by virtue of containing polymerised units of one or more aliphatic unsaturated alpha-beta unsaturated carboxylic acids. Polymers of this type are described in European Patent Application No 0115694.

Other examples of polymers usable when component (a) is a film forming binder system are copolymers of (i) vinyl chloride, (ii) vinylidene chloride and (iii) one or more alkyl acrylates or alkyl methacrylates having from 1 to 12 carbon atoms in the alkyl group; such polymers may optionally also contain polymerised units of one or more aliphatic alpha-beta unsaturated carboxylic acids. Copolymers of this type are described generally and specifically in the specification of UK Patent No 1558411.

Alkyd containing resins are extensively used as the film forming binder in paint systems and the composition may be one in which component (a) is a film forming binder system which is, or contains, an alkyd containing resin, particularly an oil-modified alkyd.

The polymer or polymers which is, or are, used when component (a) is a film forming binder system, is usually used in an amount of from 5 to 60% (based on weight in grams of the polymers per 100 cm$^3$ of the composition), and more usually 10 to 40%. The polymer may be dissolved or colloidally dispersed (that is exist as an emulsion, with an average particle size usually below two micrometers) in a suitable liquid carrier medium.

Component (a) may be any material which can be contacted with a surface either to provide a coating thereon or to provide lubrication. Thus, component (a) may be a natural oil or grease which has been derived from animals or plants, such as, for example, lanolin or rape seed oil. Alternatively, component (a) may be a petroleum refined product such as a lubricating oil, turbine oil, fuel oil, gasoil or grease, which are used in circumstances in which they contact if only temporarily, a metal surface.

The compound or composition of the present invention can be used to coat metals.

When the composition is to be used to coat a metal surface, the compound of general formula (I) will normally be used in dilute concentration, especially in a water-containing composition, and usually at 0.01 to 5% by weight of a compound of formula (I). It is preferred from a practical standpoint to use a water-containing compositions containing 0.01 to 2% by weight of a compound of formula (I). We have found that particularly useful effects have been obtained by applying water-containing compositions containing between 0.01 and 0.3% by weight of a compound of formula (I).

It will be appreciated that compositions containing greater amounts of a compound of general formula (I) may be beneficial in certain circumstances, such as transportation or storage. In such circumstances, compositions containing up to 30% of a compound of formula (I) may be preferred.

As a further aspect of the present invention there is provided a process which comprises contacting the surface of a metal with a compound of general formula (I) or a composition containing a compound of general formula (I).

The composition of the present invention is particularly useful to deposit a corrosion inhibiting coating and/or adhesion promoting coating on a metal surface.

The use of the composition of the present invention to provide a corrosion inhibiting coating may be combined with a conventional corrosion inhibition treatment such as, for example, the phosphating of iron. Furthermore, the composition may include, in addition to the compound which is component (b), other materials, particularly those which have been proposed as corrosion inhibitors. Thus, the composition may include a metal oxide or as an alternative to, or in addition to, the metal oxide, the composition may also include a metal phosphate, particularly a phosphate of the metal which is present in the metal oxide.

Thus, as a further aspect of the present invention the composition may also include at least one of a metal oxide and a metal phosphate.

In addition to the compound of formula (I) and the liquid solvent or dispersant or the surface coating composition, the composition may include various other ingredients such as those commonly employed in the film forming coating compositions such as defoamers, rheology control agents, thickeners, dispersing and stabilising agents (usually surfactants), wetting agents, extenders, fungicides, pigments or colorants of one sort or another, coalescing solvents, plasticisers, and antifreeze agents. Furthermore, as noted previously herein, the composition may also include one or more known corrosion inhibitors.

The composition of the present invention may be prepared using any one of the techniques which have been used for incorporating solids into a liquid or plastic medium in which the solid is essentially insoluble. Thus, if component (a) is a film forming coating composition, techniques for preparing paint compositions may be used, for example by mixing components either in a grinding apparatus or pre-mixing the components and then grinding. The compound of the present invention and any optional metal oxide, metal phosphate or other corrosion inhibitor, may be incorporated into the surface coating composition at any convenient stage, for example during the grinding together of the components of the paint formulation.

In one embodiment of the invention, the metal surface which is to be treated with the composition of the present invention, is first cleaned to remove greases and oils. This may be achieved by immersion in a suitable solvent or in the vapour of the solvent. An example of a suitable solvent is 1,1,1-trichloroethane. The metal surface may also be cleaned in aqueous compositions containing other cleaning agencies such as Ridolene (TM), which is an alkaline cleaning composition commercially available from ICI Paints Division. In most instances, the metal surface is finally rinsed in water prior to treatment with the composition of the present invention. It is, however, preferable to thoroughly dry the metal surface prior to treatment with the composition. This may be conveniently achieved in an oven or in a current of hot air.

The composition of the present invention may be applied to the surface of a metal by any convenient method such as spraying, dipping or painting. This can be carried out at any temperature, but is typically between 20° and 60° C. The time of treatment is relatively unimportant since the compound of general formula (I) fixes fairly rapidly with the metal surface. Thus, treatment times of less than 5 minutes can be used, for example between 0.5 and 1 minute.

Metals which can be treated with the present composition include both ferrous and non-ferrous metals. Typically, they include zinc, iron, aluminium, tin, copper and their alloys. The metal may be of any physical shape, and includes cold-rolled, ground, pickled and hot-rolled steel. The metal may be of any form such as sheet, tube, roll and especially coil. Particularly important are zinc, zinc-coated steel, and phosphated steels.

After application of the composition according to the present invention, the coated surface may be dried directly, or preferably rinsed in order to remove excess non-bonded compound of formula (I) and then dried. The metal surface may then be subsequently painted or coated. This may be achieved by brush, spray, electrostatic coating, dipping, roller coating as well as electro coating. The metal surface so treated has improved corrosion resistance and paint adhesion. The coating also improves the adhesion when conventional adhesives are used to bond one such coated surface to another.

When the composition of the present invention is used as a temporary passivation coating, especially in the case of zinc and zinc-coated steel, the coating may be substantially removed by treatment in an alkaline liquor. In this manner a fresh clean surface may be presented for subsequent processing.

A further feature of the present invention is a metal surface treated with the composition of the present invention having an improved resistance to corrosion.

Thus, as a yet further feature of the present invention there is provided a metal article, at least part of one surface of which has a coating of the compound of formula I as hereinbefore defined or which is a composition as hereinbefore described and which contains a compound of formula I as hereinbefore defined.

The surface of the metal is preferably coated with a composition which contains the compound of formula I and a known corrosion inhibitor.

As a further aspect of the invention, the compounds of general formula (I) may, in addition to providing corrosion inhibition, also give improved anti-wear characteristics when incorporated into an oil or grease which is in contact with moving metal surfaces. Thus, there is provided a lubricant composition comprising an oil or grease and a compound of general formula (I) in accordance with the present invention. The compound of general formula (I) is typically present in the lubricant composition in an amount from 0.1 up to 10% by weight, preferably 0.1 to 6% by weight and more especially 0.1 to 2% by weight.

Certain of the compounds used in the compositions of the present invention are novel.

Thus, according to a still further aspect of the invention, there are provided compounds of general formula (III)

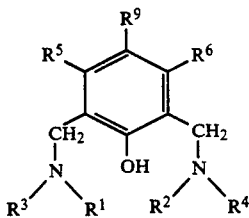

(III)

wherein:
$R^9$ is hydrogen, halogen, hydrocarbyl, hydrocarbyloxy, hydrocarbylcarbonyl, hydrocarbylsulphonyl, hydrocarbylamino, hydrocarbylamido, hydrocarbyloxycarbonyl or hydrocarbylcarbonyloxy, wherein the hydrocarbyl moiety contains up to 50 carbon atoms and may be substituted by one or more hydroxy, halogen, mercapto, ether, thioether, carbonyl, sulphonyl, nitro, cyano or ester groups or mixtures thereof;

$R^1$ and $R^2$ are, independently, amino lower alkyl, mercapto lower alkyl, and hydroxy lower alkyl;

$R^3$ and $R^4$ are, independently, hydrogen, alkyl or substituted alkyl; and $R^5$ and $R^6$ are, independently, hydrogen, halogen or lower alkoxy, or one or both of $R^5$ and $R^6$ together with $R^9$ and the two ring carbon atoms may themselves form an optionally substituted ring system, and preferably, $R^5$ and $R^6$ are both hydrogen; with the proviso that when $R^9$ is hydrogen, linear nonyl or linear dodecyl and $R^5$ and $R^6$ are both hydrogen,
$R^1$ to $R^4$ are not all 2-hydroxyethyl; or when
$R^1$ and $R^2$ are both 2-hydroxyethyl, $R^3$ and $R^4$ are not both hydrogen; or provided that when $R^9$ is linear nonyl, $R^1$ to $R^4$ are not all 3-hydroxypropyl.

Preferably $R^1$ and $R^2$ are both the same. Preferably $R^3$ and $R^4$ are both the same.

In one preferred embodiment, $R^1$, $R^2$, $R^3$ and $R^4$ are all the same.

In another preferred embodiment, where $R^9$ is hydrocarbyl it is an alkyl chain containing up to 12 and especially not more than 10 carbon atoms. These chains may be linear or branched, and may also be mixtures. Particularly important are the mixed alkyl isomers which are commercially available as alkyl phenols. As specific examples of preferred alkyl groups, there may be mentioned methyl, ethyl, n-butyl, t-butyl, t-octyl, n-heptyl, n-octyl and isomeric mixed nonyl.

The substituted lower alkyl groups as represented by $R^1$ and $R^2$ are those containing up to 4 carbon atoms. When $R^1$ and $R^2$ are substituted alkyl it is preferably hydroxy lower alkyl. Examples of hydroxy lower alkyl, are 2-hydroxyethyl and 2-hydroxypropyl. Examples of amino lower alkyl and mercapto lower alkyl are 2-aminoethyl and 2-mercaptoethyl.

Where $R^3$ and $R^4$ are alkyl or substituted alkyl, the alkyl group may contain up to 12 carbon atoms, and especially up to 8 carbon atoms. It is particularly preferred that the alkyl or substituted alkyl group contains up to 4 carbon atoms, and is particularly methyl or ethyl, 2-hydroxyethyl, 2-mercaptoethyl, 2-aminoethyl or 2-hydroxypropyl.

Lower alkoxy as represented by $R^5$ and $R^6$ refers to substituents containing up to 4 carbon atoms and includes methoxy and ethoxy.

The term halogen includes fluorine, chlorine and bromine, especially chlorine.

As examples of compounds formed when $R^5$ and/or $R^6$ together with R and the ring carbon atoms to which they are attached form a ring, there may be mentioned derivatives of hydroxyquinoline, nophthols, and hydroxytetrahydroquinolines.

In a yet further embodiment of the present invention, there is provided a compound having a substituted hydrocarbyl, substituted hydrocarbyloxy, substituted hydrocarbylcarbonyl or substituted hydrocarbylsulphonyl group and wherein, the substituent itself is a derivative of 2,6-bis(substituted aminomethyl)phenol. Accordingly, there are provided compounds of general formula (II)

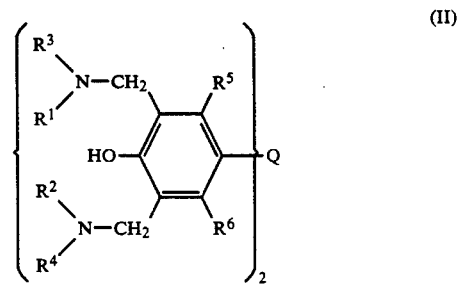

(II)

wherein
$R^1$ to $R^6$ and Q are all as previously defined for the composition containing a compound of general formula (II).

An specific examples, there may be mentioned those compounds of general formula (III) where $R^1$ and $R^2$ are both 2-hydroxyethyl, $R^3$ and $R^4$ are both methyl or 2-hydroxyethyl and $R^5$ and $R^6$ are both hydrogen. These include 2,6-bis(N-2-hydroxyethyl-N-methylaminomethyl)-4-nonylphenol 2,6-bis(N-2-hydroxyethyl-N-methylaminomethyl)-4-t-octylphenol 2,6-bis(N-2-hydroxyethyl-N-methylaminomethyl)-4-dodecylphenol 2,6-bis(N-2-hydroxyethyl-N-methylaminomethyl)-4-t-butylphenol 2,6-bis(N-2-hydroxyethyl-N-methylaminomethyl)-4-ethylphenol, and 2,6-bis[N,N-di(2-hydroxyethyl)aminomethyl]-4-t-octylphenol.

As specific examples of compounds of general formula (II) there may be mentioned 2,2-bis[3,5-bis(N-2-hydroxyethyl-N-methylaminomethyl)-4-hydroxyphenyl]propane (Q is dimethyl methylene), and analogues derived from 4,4'-dihydroxybiphenyl (Q is a direct bond), 4,4'-dihydroxydiphenyl sulphone (Q is sulphonyl) and 4,4'-dihydroxy benzophenone (Q is carbonyl).

The compounds of general formula (I), (II) and (III) may be made be any method known to those skilled in the art. Typically, they are made using a Mannich reaction whereby one mole equivalent of a phenol which is unsubstituted in both the 2 and 6 positions is reacted with at least 2 mole equivalents of an alkylamine in the presence of excess formaldehyde. In the case of bisphenols, the ratio of the alkylamine is retained at 2 or more moles per each equivalent of the phenol moiety.

In one particular embodiment of the invention, where R of general formula (I) is hydrogen, the phenol may be reacted with at least 3 equivalents of the alkylamine in the presence of excess formaldehyde to give a 2,4,6-trisubstituted alkylamino methyl phenol.

Examples of phenols which are suitable as starting intermediates include 4-ethylphenol, 4-t-butyl phenol, 4-octyl phenol, 2-naphthol, bis-(4-hydroxyphenyl)propane and related bis-phenols.

The alkylamines are preferably hydroxyalkylamines especially diethanolamine, 2-(methylamino)ethanol, and 2-aminopropanol.

Various aspects of the present invention are set out in more detail hereafter in the following illustrative examples in which all parts and percentages are by weight unless otherwise stated.

For comparative purposes, the following mono substituted 4-alkylphenols were prepared by the method described in EP 276072. Thus, Compounds F, E and D were prepared as described in examples 1,2 and 3 respectively of EP 276072. The other compounds were prepared by analogous methods.

Compound A 2-(N-2-hydroxyethyl-N-methylaminomethyl)-4-nonylphenol, By analysis:

| $C_{19}H_{33}NO_2$.1H$_2$O | requires | 69.9% C, | 10.8% H, | 4.3% N |
|---|---|---|---|---|
| | Found | 69.9% C, | 10.5% H, | 3.4% N |

Analysis by Proton NMR was consistent with the proposed structure.

Compound B 2-(N-2-hydroxyethyl-N-methylaminomethyl)-4-t-octylphenol, By analysis:

| $C_{18}H_{31}NO_2$.2H$_2$O | requires | 72.7% C, | 10.6% H, | 4.7% N |
|---|---|---|---|---|
| | Found | 72.7% C, | 10.9% H, | 3.9% N |

NMR analysis gave the following results:
Proton NMR: $\delta$(CDCl$_3$): 0.75 (s, 9H, (CH$_3$)$_3$—); 1.35 (s, 6H, —C—(CH$_3$)$_2$); 1.70 (s(broad), 2H, C—CH$_2$—C); 2.30 (s, 3H, N—CH$_3$); 2.60 (t(broad), 2H, —CH$_2$—O—); 3.70 (s(broad), 4H, (—CH$_2$—N)$_2$); 6.7 to 7.3 (m, 3H, aromatic protons); 7.35 (s, approximately 2H, exchanges with D$_2$O, (—OH)$_2$)

Compound C 2-(N-2-hydroxyethyl-N-methylaminomethyl)-4-dodecylphenol, By analysis:

| $C_{22}H_{39}NO_2$ | requires | 75.7% C, | 11.2% H, | 4.0% N |
|---|---|---|---|---|
| | Found | 75.7% C, | 11.4% H, | 3.4% N |

Analysis by Proton NMR was consistent with the proposed structure.

Compound D 2-(N-2-hydroxyethyl-N-methylaminomethyl)-4-t-butylphenol, By analysis:

| $C_{14}H_{23}NO_2$ | requires | 70.9% C, | 9.7% H, | 5.9% N |
|---|---|---|---|---|
| | Found | 70.8% C, | 10.2% H, | 5.1% N |

Analysis by Proton NMR was consistent with the proposed structure.

Compound E 2-(N-2-hydroxyethyl-N-methylaminomethyl)-4-ethylphenol, By analysis:

| $C_{12}H_{19}NO_2$.0.2H$_2$O | requires | 67.7% C, | 9.1% H, | 6.6% N |
|---|---|---|---|---|
| | Found | 67.7% C, | 9.3% H, | 6.1% N |

Analysis by Proton NMR was consistent with the proposed structure.

Compound F 2,2-bis(4,4$^1$-dihydroxy-3,3$^1$-bis(N-2-hydroxyethyl-N-methylaminomethyl))phenylpropane, By analysis:

| $C_{23}H_{34}N_2O_4$.0.75H$_2$O | requires | 66.4% C, | 8.5% H, | 6.7% N |
|---|---|---|---|---|
| | Found | 66.7% C, | 8.9% H, | 5.2% N |

Analysis by Proton NMR was consistent with the proposed structure.

Compound G

2-[N,N-di(2-hydroxyethyl)aminomethyl]-4-t-octylphenol, By analysis:

| $C_{19}H_{33}NO_3$ | requires | 66.2% C, | 9.6% H, | 4.1% N |
|---|---|---|---|---|
| | Found | 66.2% C, | 10.0% H, | 4.5% N |

Analysis by Proton NMR was consistent with the proposed structure.

EXAMPLE 1

A solution containing 4-nonylphenol (mixed isomers, 55 parts), N-methylethanolamine (39 parts), water (40 parts) and industrial methylated spirits (100 parts) was stirred and heated to between 50° and 55° C. Formaldehyde (37% solution in water, 40 parts) was slowly added over 45 minutes, maintaining the temperature below 60° C. throughout. The reaction mix was then heated to the boil (85° C.) and stirred at the boil under reflux for 20 hours when High Performance Liquid Chromatography indicated the reaction to be complete.

The reaction mix was cooled to 50° C. and the industrial methylated spirit removed under reduced pressure (20-25 Torr) using a rotary evaporator. The product was then dissolved in carbon tetrachloride (300 parts), and the solution washed with three successive portions (100 parts each) of cold water. A solution of sulphuric acid (20 parts) in water (180 parts) was added and the mixture shaken vigourously. The aqueous acidic layer was then separated, and washed with carbon tetrachloride (200 parts). The aqueous acidic layer was then treated with carbon tetrachloride (300 parts), and the aqueous layer neutralised by adding 5N sodium hydroxide solution (approximately 80 parts). After shaking vigourously, the lower organic phase was separated and washed with two successive portions (100 parts) of cold water. The organic phase was then dried over anhydrous magnesium sulphate, and the carbon tetrachloride removed under reduced pressure (20–25 Torr) to leave a pale yellow oil. This was further dried in vacuo over anhydrous calcium chloride at 20–25 Torr and 20°±5° C. to give 70.0 parts of a pale yellow oil.

By analysis:
2,6-bis(N-2-hydroxyethyl-N-methylaminomethyl)-4-nonylphenol,

| | | | | |
|---|---|---|---|---|
| $C_{23}H_{42}N_2O_3 4.4H_2O$ | requires | 58.4% C, | 8.6% H, | and 5.9% N |
| | Found | 58.4% C, | 8.8% H, | and 5.4% N |

NMR analysis gave the following results:
Proton NMR: $\delta(CDCl_3)$: 0.4 to 1.8 (m, ca.19H, mixed $C_9H_{19}$ alkyls); 2.30 (s,6H, (N—$CH_3$)$_2$); 2.6 t(broad), 4H, (—$CH_2O$)$_2$); 4.0 (s(broad), 8H, (—$CH_2$—N—$CH_2$—)$_2$); 6.8 (s(broadened), 3H, exchanges with $D_2O$, (OH)$_3$); 7.2 (d,2H, m—coupled aromatic protons).

EXAMPLE 2

Example 1 was repeated except the 4-nonylphenol was replaced with 4-t-octylphenol (51.5 parts). The product was purified using chloroform in place of the carbon tetrachloride used in example 1. A pale yellow oil was again obtained (85.67 parts). By analysis:
2,6-bis(N-2-hydroxyethyl-N-methylaminomethyl)-4-t-octylphenol,

| | | | | |
|---|---|---|---|---|
| $C_{22}H_{40}N_2O_3$ | requires | 55.8% C, | 8.4% H, | 5.9% N |
| | Found | 55.8% C, | 8.8% H, | 5.0% N |

NMR analysis gave the following results:
Proton NMR: $\delta(CDCl_3)$: 0.75 (s, 9H, ($CH_3$)$_3$C—); 1.35 (s, 6H, ($CH_3$)$_2$—C—Ph); 1.70 (s, 2H, —C—$CH_2$—C—); 2.20 (s, 6H, ($CH_3$—N)$_2$); 2.60 (s(broad), 4H, ($CH_2OH$)$_2$); 3.70 (s(broad), 8H, ($CH_2$—N)$_4$); 6.60 (s, ca. 3H, exchanges with $D_2O$, (—OH)$_3$); 7.0 (s, 2H, aromatic protons).

EXAMPLE 3

Example 2 was repeated except 4-dodecylphenol (mixed isomer alkyl chain, 65.5 parts) was used in place of the 4-t-octylphenol. A pale yellow oil was again obtained (103.72 parts). By analysis:
2,6-bis(N-2-hydroxyethyl-N-methylaminomethyl)-4-dodecylphenol,

| | | | | |
|---|---|---|---|---|
| $C_{26}H_{48}N_2O_3 2.5H_2O$ | requires | 64.8% C, | 11.0% H, | 5.8% N |
| | Found | 64.8% C, | 10.3% H, | 4.8% N |

NMR analysis gave the following results:
Proton NMR: $\delta(CDCl_3)$: 0.6 to 2.0 (m, ca.25H, branched alkyl chain); 2.5 (s,6H, ($CH_3$—N)$_2$); 2.8 (s(broad), 4H, (—$CH_2$—OH)$_2$); 3.80 (s(broad), 8H, ($CH_2$—N)$_4$); 6.80 s, ca.3H, exchanges with $D_2O$, (—OH)$_3$); 7.2 (s (broad), 2H, aromatic protons).

EXAMPLE 4

Example 2 was repeated except 4-t-butylphenol (37.5 parts) was used in place of the 4-t-octylphenol. A pale yellow oil was obtained (36.84 parts).
By analysis:
2,6-bis(N-2-hydroxyethyl-N-methylaminomethyl)-4-t-butylphenol,

| | | | | |
|---|---|---|---|---|
| $C_{18}H_{32}N_2O_3 2.4H_2O$ | requires | 58.9% C, | 10.0% H, | 7.6% N |
| | Found | 58.9% C, | 8.9% H, | 6.8% N |

NMR analysis gave the following results:
Proton NMR: $\delta(CDCl_3)$: 1.50 (s, 9H, ($CH_3$)$_3$—C—); 2.60 (s, 6H, ($CH_3$—N)$_2$); 2.80 (t(broad), 4H, ($CH_2OH$)$_2$); 3.90 (s(broad), 8H, ($CH_2$—N)$_4$); 6.80 (s, ca.3H, exchanges with $D_2O$, (—OH)$_3$); 7.30 (s, 2H, aromatic protons).

EXAMPLE 5

Example 2 was repeated except 4-ethylphenol (30.5 parts) was used in place of the 4-t-octylphenol. A pale yellow oil was obtained (40.54 parts).
By analysis:
2,6-bis(N-2-hydroxyethyl-N-methylaminomethyl)-4-ethylphenol,

| | | | | |
|---|---|---|---|---|
| $C_{16}H_{28}N_2O_3 0.65H_2O$ | requires | 62.4% C, | 9.5% H, | 9.1% N |
| | Found | 62.4% C, | 9.1% H, | 7.2% N |

NMR analysis gave the following results:
Proton NMR: $\delta(CDCl_3)$; 1.2(t, 3H—$CH_2CH_3$); 2.3(s, 6H, (N—$CH_3$)$_2$); 2.6(m, 6H, (—$CH_2O$)$_2$ and ($CH_2CH_3$)); 3.6(m, 8H, (N—$CH_2$)$_4$); 6.6(s, (broad), approx 3H, exchanges with $D_2O$, (—OH)$_3$); 6.9(s(broad), 2H, aromatic protons).

EXAMPLE 6

2,2-bis(4-hydroxyphenyl)propane (bisphenol A, 11.2 parts) was stirred with industrial methylated spirit (50 parts) and water (15 parts). N-methylethanolamine (16.5 parts, 4.1 molar equivalents) was added and the mixture stirred at between 55° and 60° C. Formaldehyde (37% solution in water, 16.5 parts) was added over 1 hours. The temperature was then raised to the boil, and the reaction mix stirred at the boil under reflux for 16 hours. The water and industrial methylated spirit were then removed under reduced pressure (20–25 Torr) at a maximum temperature of 70° C. to give a yellow oil (33 parts). By analysis:
2,2-bis[3,5-bis(N-2-hydroxyethyl-N-methylaminomethyl)-4-hydroxyphenyl]propane,

| | | | | |
|---|---|---|---|---|
| $C_{31}H_{52}N_4O_6 3.6H_2O$ | requires | 58.0% C, | 9.2% H, | 8.7% N |
| | Found | 58.0% C, | 9.4% H, | 8.6% N |

NMR analysis gave the following results:
Proton NMR: $\delta(CDCl_3)$: 1.55(s, 6H, (—$CH_3$)$_2$); 2.2(s, 12H, ($CH_3$—N)$_4$); 2.5(m, 8H, ($CH_2$—O)$_4$); 3.6(s(broad), 16H, ($CH_2NCH_2$)$_4$); 6.0(s(broad), approx 6H, exchanges with $D_2O$, (—OH)$_6$); 6.8(s (broad), 4H, aromatic protons)

EXAMPLE 7

A solution containing t-octylphenol (41.2 parts) and diethanolamine (63 parts) in industrial methylated spirit was stirred and heated to between 50° and 60° C. Formaldehyde (37% solution in water, 33 parts) was added slowly over 1 hour, whilst maintaining the temperature between 55° and 60° C. The mixture was then raised to the boil, and stirred under gentle reflux for 24 hours. Analysis of the reaction mix by high performance liquid chromatography (HPLC) indicated that the reaction mix contained equimolar amounts of the mono- and di-substituted phenol. A further charge of formaldehyde (37% aqueous solution, 11 parts) was then added and stirring at the boil continued for a further 24 hours. Analysis by HPLC showed the reaction to be approximately 85% complete. A further charge of aqueous formaldehyde (5.5 parts) was added and stirring at the boil continued for a further 24 hours. HPLC analysis indicated the reaction to be essentially complete.

The reaction mix was cooled below 60° C., and the industrial methylated spirit removed under reduced pressure (20–25 Torr). The residual oil was dissolved in ethyl acetate (320 parts) and washed successively with two portions of water (200 parts). The solution of the product in ethyl acetate was then treated with aqueous 3N sulphuric acid (200 parts) and shaken vigourously. The aqueous acid layer was separated and washed with ethyl acetate (300 parts).

The aqueous layer was then neutralised to about pH 7 by adding 5N sodium hydroxide solution (approximately 100 parts), and extracted with two successive portions of ethyl acetate (200 parts each). The combined organic layers were finally washed with water (100 parts) and dried over anhydrous magnesium sulphate. The ethyl acetate was then removed under reduced pressure (20–25 Torr) to give a pale yellow oil (88.1 parts). By analysis:

2,6-bis[N,N-di(2-hydroxyethyl)aminomethyl]-4-t-octylphenol,

| $C_{24}H_{44}N_2O_5H_2O$ | requires | 62.8% C, | 10.1% H, | 6.1% N |
|---|---|---|---|---|
| | Found | 62.8% C, | 10.0% H, | 5.1% N |

NMR analysis gave the following results:
Proton NMR: $\delta(CDCl_3)$: 0.7(s, 9H, (C—(CH$_3$)$_3$)); 1.3(s, 6H, (C—(CH$_3$)$_2$)); 1.6(s, 2H, (C—CH$_2$—C)); 2.6(m, 8H, (CH$_2$—O)$_4$); 3.6(m(broad), 12H, (—(CH$_2$)$_2$N—)$_2$); 5.8(s(broad), approx 5H, exchanges with D$_2$O, (—OH)$_5$); 7.0(s(broad), 2H, aromatic protons).

EXAMPLE 8

Phenol (18.8 parts), N-methylethanolamine (50 parts) and water (30 parts) were stirred and heated to 80° C. Formaldehyde (37% aqueous solution, 46.5 parts) was added over 1 hour whilst maintaining a temperature between 80° and 85° C. The temperature was then raised to between 90° and 95° C. and stirring continued for a further 16 hours. The water was then removed by distillation under reduced pressure (20–25 Torr), and the resulting clear pale yellow oil dried in vacuo at 18 to 20 Torr and 60° C. for 24 hours. 32.1 parts oil were obtained. By analysis:

2,4,6-tri-(N-2-hydroxyethyl-N-methylaminomethyl)-phenol,

| $C_{18}H_{33}N_3O_4 1.1H_2O$ | requires | 57.6% C, | 9.4% H, | 11.2% N |
|---|---|---|---|---|
| | Found | 57.6% C, | 9.3% H, | 10.8% N |

Analysis by Proton NMR was consistent with the proposed structure.

EXAMPLE 9

Samples of zinc-coated steel obtained from British Steel and labelled MINIMUM SPANGLE GALVATITE were cut into coupons measuring 10.16 by 2.54 cms. These coupons were cleaned by successive immersion in a) boiling 1,1,1-tri-chloroethane liquid for 5 minutes, b) the vapour above boiling 1,1,1-trichloro-ethane for 20 seconds, c) an aqueous solution of Ridolene 1089 (15 gm/l.) for 10 seconds at 60° C., d) cold running tap water, and e) cold distilled water. The coupons were then dried in a current of warm air for 30 seconds.

Three coupons so cleaned were each immersed in a solution containing approximately 0.02 "ligin" concentration of a compound of general formula (I) or (II) for 5 minutes at 25° C. The coupons were then removed, allowed to drain for 30 seconds and dried in a current of warm air. The edges of each coupon were then coated with a protective film of butyl rubber and the paint allowed to dry at 25° C. Each of the coupons was then separately immersed in distilled water in a glass jar, and allowed to stand at a temperature between 20° and 25° C. The extent of corrosion of each coupon as percentage of the area corroded was estimated visually at regular intervals.

The term "ligin" used above is defined as the molar concentration of the chelant divided by the number of chelating moieties in the molecule. Thus, in the case of the mono substituted phenols used for comparison, the number of chelating centres is taken as 3 for those compounds derived from N-methylamino-ethanol i.e. one phenolic hydroxyl, one hydroxyl group on the alkyl chain and one nitrogen atom attached to the methylene group. In similar manner, the "ligin" used for the mono-substituted chelants derived from diethanolamine is the molar concentration divided by 4. i.e. one phenolic hydroxyl, two hydroxyl groups on the alkyl chain and one nitrogen atom attached to the methylene group.

The "ligin" concentration of the chelants used in the present compositions have been calculated in similar fashion.

The amount of the various chelants used is displayed in Table 1. These amounts were separately dissolved in propan-2-ol using the volume indicated in the table. A portion of distilled water was then added, and the pH adjusted to about pH 4.7 by addition of 5N phosphoric acid. The volume was then finally adjusted to give the required concentration by addition of distilled water. The amount of propan-2-ol and total amount of water used in each case is displayed in Table 1.

The degree of corrosion of each of the coupons is detailed in Table 2. These figures indicate the time taken for the whole of the surface to become corroded. The controls included in Table 2 were prepared by immersing the cleaned coupons for 5 minutes in aqueous propan-2-ol solutions where the pH had been adjusted to pH 4.7 with phosphoric acid. The coupons were allowed to drain and were finally dried in a current of warm air as before.

TABLE 1

| Chelant used | parts by weight | propan-2-ol parts by vol. | final volume by adding water |
|---|---|---|---|
| Example 1 | 0.247 | 15 | 154 |
| Compound A | 0.696 | 30 | 325 |
| Example 2 | 0.318 | 20 | 199 |
| Compound B | 0.232 | 12 | 116 |
| Example 3 | 0.250 | 13 | 139 |
| Compound C | 0.305 | 15 | 127 |
| Example 4 | 0.197 | 15 | 152 |
| Compound D | 0.433 | 27 | 270 |
| Example 5 | 0.295 | 24 | 246 |
| Compound E | 0.165 | 16 | 118 |
| Example 6 | 0.165 | 14 | 138 |
| Compound F | 0.235 | 17 | 168 |
| Example 7 | 0.150 | 30 | 120 |
| Compound G | 0.190 | 30 | 120 |

TABLE 1-continued

| Chelant used | parts by weight | propan-2-ol parts by vol. | final volume by adding water |
|---|---|---|---|
| Example 8 | 0.242 | 17 | 173 |

TABLE 2

| Chelant used | Time to become 100% covered in corrosion products (hrs) | | | Mean corrosion time (hrs) |
|---|---|---|---|---|
| Example 1 | 450 | 450 | 500 | 467 |
| Compound A | 150 | 186 | 280 | 205 |
| Example 2 | 150 | 280 | 280 | 237 |
| Compound B | 114 | 114 | 150 | 126 |
| Example 3 | 500 | 500 | 625 | 542 |
| Compound C | 336 | 625 | 625 | 529 |
| Example 4 | 280 | 280 | 280 | 280 |
| Compound D | 150 | 150 | 150 | 150 |
| Example 5 | 280 | 625 | 625 | 510 |
| Compound E | 186 | 200 | 280 | 222 |
| Example 6 | 186 | 280 | 280 | 249 |
| Compound F | 114 | 150 | 200 | 155 |
| Example 7 | 400 | 650 | NT | 525 |
| Compound G | 136 | 186 | NT | 161 |
| Example 8 | 186 | 186 | 186 | 186 |
| Control 1 | 17 | 24 | 24 | 21.6 |
| Control 2 | 17 | 17 | 24 | 19.3 |

NT Not tested.

EXAMPLE 10

4.86 parts of the compound of Example 5 was dissolved in isopropanol, and the volume adjusted to 25 parts by volume. Aliquots of this solution were then diluted with distilled water to 150 parts by volume and the pH adjusted to 4.0 using 1% aqueous phosphoric acid. The volume was then made up to 200 parts by volume with distilled water. In this manner 0.001, 0.005 and 0.01 molar solutions were prepared.

Similar solutions were prepared for comparison by replacing the 4.86 parts compound of Example 5 with 3.345 parts Compound E.

MINIMUM SPANGLE GALVATITE zinc-coated steel coupons were treated with the above solutions as described in Example 9, and the corrosion resistance determined after 45 and 113 hours immersion as described in Example 9. Controls containing no chelant were prepared by treating coupons in similar solutions of aqueous isopropanol at pH 4.0. The results obtained are displayed in Table 3.

TABLE 3

| Conc. | Chelant | % surface corrosion | |
|---|---|---|---|
| | | 45 hours | 113 hours |
| 0.001M | Example 5 | 0 | 0 |
| 0.001M | " | 0 | 30 |
| 0.005M | " | 0 | 0 |
| 0.005M | " | 0 | 0 |
| 0.01M | " | 0 | 0 |
| 0.01M | " | 0 | 0 |
| 0.001M | Compound E | 60 | 100 |
| 0.001M | " | 45 | 100 |
| 0.005M | " | 0 | 80 |
| 0.005M | " | 0 | 70 |
| 0.01M | " | 0 | 0 |
| 0.01M | " | 20 | 70 |
| Control | | 100 | 100 |
| " | | 100 | 100 |

EXAMPLE 11

1 part of the compound described in Example 2 was stirred in 150 parts distilled water and the pH adjusted to 3.9 by addition of dilute aqueous phosphoric acid. The volume was then adjusted to 200 parts by addition of distilled water.

1 part Compound B was treated in similar manner.

These two solutions were then used to treat MINIMUM SPANGLE GALVATITE coupons as described in Example 9 and subjected to the immersion corrosion test as described in the said example. The results are given below.

| Chelant used | % surface corrosion | | | |
|---|---|---|---|---|
| | 72 hrs. | 96 hrs. | 170 hrs. | 264 hrs. |
| Example 2 | 0 | 0 | 0 | 0 |
| Compound B | 0 | 0 | 40 | 100 |

I claim:

1. A composition which comprises
   (a) a liquid solvent or dispersant or surface coating composition; and
   (b) from 0.01 to 30% by weight of the composition of a 2,6-bis(substituted aminomethyl)phenol of formula (I)

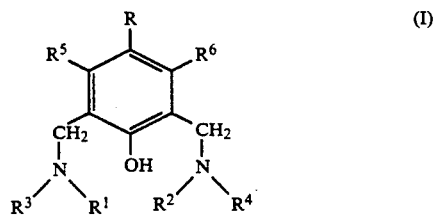

wherein:

R is hydrogen, halogen, hydrocarbyl, hydrocarbyloxy, hydrocarbylcarbonyl, hydrocarbylsulphonyl, hydrocarbylamino, hydrocarbylamido, hydrocarbyloxycarbonyl or hydrocarbylcarbonyloxy, wherein hydrocarbyl in each instance contains up to 50 carbon atoms and may be substituted by one or more hydroxy, halogen, amino, mercapto, ether, thioether, carbonyl, sulphonyl, nitro, cyano or ester groups or a mixture thereof;

$R^1$ and $R^2$ are, independently, amino lower alkyl, mercapto lower alkyl or hydroxy lower alkyl;

$R^3$ and $R^4$ are, independently, hydrogen or alkyl, as defined for $R^1$ and $R^2$; and $R^5$ and $R^6$ are, independently, hydrogen, halogen or lower alkoxy, or one or both of $R^5$ and $R^6$ together with R and the two ring carbon atoms to which $R^5$ and $R^6$ are attached form a ring system.

2. The composition of claim 1 wherein the hydrocarbyl is a linear or branched alkyl chain containing up to 12 carbon atoms.

3. The composition of claim 1, where R is a group $-CH_2NR^7R^8$ where $R^7$ and $R^8$ are, independently, hydrogen or alkyl, as defined for $R^1$ and $R^2$, provided that at least one of $R^7$ and $R^8$ is not hydrogen.

4. The composition of claim 1, where the 2,6-bis(substituted aminomethyl)phenol is a compound of formula (II)

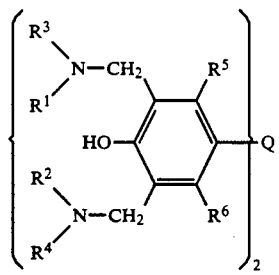

(II)

wherein:
R⁵ and R⁶ are, independently, hydrogen, halogen or alkoxy; and
Q is a direct bond, lower alkylene, substituted lower alkylene group, an oxygen atom or a carbonyl or sulphonyl group.

5. The composition of claim 1, where $R^1$ and $R^2$ are 2-hydroxyethyl or 2-hydroxypropyl.

6. The composition of claim 1, where $R^3$ and $R^4$ are, independently, amino lower alkyl, mercapto lower alkyl or hydroxy lower alkyl.

7. A process which comprises coating a metal surface with a composition as claimed in claim 1 so that from 0.01 to 5% of component (b) is applied to the surface.

* * * * *